United States Patent
Todo et al.

(10) Patent No.: US 6,756,421 B1
(45) Date of Patent: Jun. 29, 2004

(54) DENTAL GLASS IONOMER CEMENT COMPOSITION

(75) Inventors: Atsuhiro Todo, Tokyo (JP); Kaori Okada, Tokyo (JP); Toshihiro Sekiguchi, Tokyo (JP); Kazuo Hirota, Tokyo (JP)

(73) Assignee: GC Corporation, Tokyo (JP)

( * ) Notice: Subject to any disclaimer, the term of this patent is extended or adjusted under 35 U.S.C. 154(b) by 126 days.

(21) Appl. No.: 09/690,731

(22) Filed: Oct. 18, 2000

(30) Foreign Application Priority Data

Oct. 20, 1999 (JP) ............................................. 11-297966

(51) Int. Cl.[7] .............................. A61K 6/08; C08K 3/34; C08K 3/22; C08K 5/00
(52) U.S. Cl. ......................... 523/116; 523/115; 524/81; 524/88; 524/431; 524/492
(58) Field of Search ................................ 323/116, 115; 524/81, 431, 88, 492

(56) References Cited

U.S. PATENT DOCUMENTS

| | | | | |
|---|---|---|---|---|
| 4,678,436 A | * | 7/1987 | Kondo et al. | |
| 5,312,863 A | * | 5/1994 | Van Rheenen et al. | |
| 5,436,049 A | * | 7/1995 | Hu | |
| 5,503,665 A | * | 4/1996 | Miller et al. | |
| 5,844,019 A | * | 12/1998 | Kato | |
| 5,965,632 A | * | 10/1999 | Orlowski et al. | |
| 6,191,191 B1 | * | 2/2001 | Harada et al. | |
| 6,270,214 B1 | * | 8/2001 | Smith et al. | |

FOREIGN PATENT DOCUMENTS

| | | |
|---|---|---|
| EP | 0 389 239 A1 | 9/1990 |
| WO | WO 88/01859 A1 | 3/1988 |
| WO | WO 95/22956 A1 | 8/1995 |

OTHER PUBLICATIONS

WPI Abstract AN: 1999–366968 [31] & JP 11139920 A.

* cited by examiner

Primary Examiner—Tae H. Yoon
(74) Attorney, Agent, or Firm—Oblon, Spivak, McClelland, Maier & Neustadt, P.C.

(57) ABSTRACT

A dental glass ionomer cement composition is disclosed, containing a coloring matter, a color of which is specified such that an L* value, when expressed by an L*a*b* colorimetric system in a standard illuminant $D_{65}$, being 60 or less, and a content of the coloring matter being preferably from 0.1 to 5% by weight based on the whole of the composition, and when the dental glass ionomer cement composition according to the invention is used in a setting method of a dental glass ionomer cement that is a most generally used dental cement at present over a wide range of dental applications by means of irradiation with a light, it has an effect for further shortening the time of sensitization to water and the time of setting.

4 Claims, No Drawings

DENTAL GLASS IONOMER CEMENT COMPOSITION

BACKGROUND OF THE INVENTION

1. Field of the Invention

The present invention relates to a dental glass ionomer cement composition to be used for dental restoration or prevention.

2. Conventional Art

In general, dental cements are used in a number of types for the dental remedy. Representative examples include a zinc phosphate cement in which zinc oxide is reacted with phosphoric acid, a carboxylate cement in which zinc oxide is reacted with a polycarboxylic acid, a resin cement in which polymerization of an acrylic monomer is used, a calcium hydroxide cement in which calcium hydroxide is reacted with an oily component, a zinc oxide eugenol cement in which zinc oxide is reacted with eugenol, and a glass ionomer cement using a fluoroaluminosilicate glass powder and a polycarboxylic acid.

These dental cements are used in a wide range in the dental remedy. There are applications in a wide range in, for example, a luting cement for cementing a dental prosthesis, such as crown, inlay, and bridge to a tooth or for cementing an orthodontic appliance to a tooth; a filling cement for filling a dental cavity; a sealant cement for sealing pit and fissure in posterior teeth; a lining cement for lining a cavity; and a cement for core construction.

Of these dental cements, the dental glass ionomer cement has a superior affinity to living bodies and has adhesive properties to a tooth structure, and a set product thereof has translucence and is superior in esthetics. In addition, the dental glass ionomer cement has such an advantage that after set, it releases gradually fluorine ions with a lapse of time, whereby it can be expected to have a caries preventing function. Therefore, the dental glass ionomer cement is a dental cement that is most generally used at present over a wide range of dental applications.

This dental glass ionomer cement is a dental cement comprising, as major components, a fluoroaluminosilicate glass powder, a polycarboxylic acid and water. Specifically, the dental glass ionomer cement is a dental cement in which an aqueous solution of polyacrylic acid acts to the fluoroaluminosilicate glass powder to liberate metal ions (alkali metal ions, alkaline earth metal ions, and aluminum ions) in the glass, and the liberated metal ions undergo ionic bonding to a carboxyl group of the polyacrylic acid to form a crosslinking structure, whereby the cement is gelled for setting (such reaction being sometimes referred to "ionomer reaction", hereinafter).

In addition, nowadays, a resin-reinforced dental glass ionomer cement is developed in which a dental glass ionomer cement is compounded with a polymerizable monomer, and a polymerization reaction of the monomer is used in combination with the ionomer reaction. This cement is improved in mechanical strengths, such as bending strength, and adhesive properties to a tooth structure, as compared with the conventional dental glass ionomer cements in which the setting is effected only by the ionomer reaction.

Since the dental glass ionomer cement uses the ionomer reaction, a time is required for effecting initial setting. Thus, it is impossible to proceed to the next clinical operation until finishing the initial setting. Further, it is pointed out that the dental glass ionomer cement has a defect called as sensitization to water: that is, before finishing the initial setting, when a surface of the dental glass ionomer cement mixture comes into contact with water, metal ions elute out during the setting reaction, or the content of water increases, whereby the cement surface becomes cloudy or brittle, ultimately leading to a decreased surface performance of the set product. This is due to an acid/base reaction between the fluoroaluminosilicate glass (base) and the polycarboxylic acid (acid radical) in the presence of water caused by the ionomer reaction of the dental glass ionomer cement, such reaction being sensitively influenced by water from the outside.

In order to overcome this defect, the following measure was hitherto taken. That is, the dental glass ionomer before the setting is carefully subjected to cementing, filling and application operations so that it does not come into contact with water such as saliva from the surface of the mixture and applied with a coating material called as a varnish such as resin-based materials, and after drying, a coating film is formed on the dental glass ionomer cement surface for from 20 to 25 minutes during the initial setting.

Further, the present inventors developed a method for setting a dental glass ionomer cement, by means of irradiation with a light to accelerate initial setting, the cement comprising fluoroaluminosilicate glass and polycarboxylic acid and water, without particularly undergoing an operation with a varnish or the like, and then filed an application for patent in Japanese Patent Application No. 226354/1999. According to this method, it is possible to suppress the influence by the sensitization to water to some extent. However, actually, it is difficult to completely suppress the influence by the sensitization to water, and therefore, the development of a more effective dental glass ionomer cement composition has been demanded.

An object of the invention is to provide a dental glass ionomer cement composition which, when applied to the inventors' previously proposed setting method of a dental glass ionomer cement by means of irradiation with a light to accelerate initial setting, the cement comprising fluoroaluminosilicate glass powder, a polycarboxylic acid and water.

Thus, the inventors have made further investigations as to a dental glass ionomer cement composition in which, when irradiated with light, a setting reaction by the ionomer reaction is promoted. As a result, it has been found that, when a coloring matter is contained in a dental glass ionomer cement composition, and a color is specified such that an $L^*$ value, when expressed by an $L^*a^*b^*$ colorimetric system in a standard illuminant $D_{65}$, is 60 or less, setting reaction has been further promoted effectively leading to accomplishment of a dental glass ionomer cement composition of the present invention.

Specifically, the dental glass ionomer cement composition according to the present invention is a dental glass ionomer cement composition comprising a coloring matter, a color of which is specified such that an $L^*$ value, when expressed by an $L^*a^*b^*$ colorimetric system in a standard illuminant $D_{65}$, is 60 or less.

In particular, it has also been found that the dental glass ionomer cement composition according to the present invention preferably has a content of the coloring matter which is from 0.1 to 5% by weight based on the whole of the composition.

DESCRIPTION OF THE PREFERRED EMBODIMENTS

The dental glass ionomer cement composition according to the present invention is a dental glass ionomer cement composition, a color of which is specified such that in a standard illuminant $D_{65}$, an L* value is 60 or less, when expressed by an L*a*b* colorimetric system, by adding a coloring matter to the conventionally used dental glass ionomer cement composed mainly of a fluoroaluminosilicate glass component, a polycarboxylic acid and water and having a mechanism in which the fluoroaluminosilicate glass component and the polycarboxylic acid cause a setting reaction (namely, the ionomer reaction) in the presence of water, whereby the cement is set. The dental glass ionomer cement composition according to the present invention is used mainly where a light having a wavelength of from 320 to 780 nm as widely used in the current dental remedy, is irradiated.

In order to color a dental glass ionomer cement composition to present a tooth, a trace amount (from about 0.001 to 0.01% by weight based on the whole of the dental glass ionomer cement composition) of a coloring matter such as $TiO_2$ and red oxide was hitherto used. However, in such conventional dental glass ionomer cement, the above-described coloring matter was used for the purpose of realizing a tooth color. For this reason, an L* value, when expressed in an L*a*b* colorimetric system in a standard illuminant $D_{65}$, was large (L*=from about 64 to 85), and the reflectance of light was large. Accordingly, when such dental glass ionomer cement is used in our previously proposed method for setting the dental glass ionomer cement, the coloring matter failed to function to exhibit an effect for improving the initial setting of the dental glass ionomer cement.

The dental glass ionomer cement composition according to the present invention has a characteristic that the temperature increases upon irradiation with light, and the time of initial setting is accelerated, whereby the influence by the sensitization to water becomes less. So, if the dental glass ionomer cement composition according to the present invention, when it is possible to irradiate with light, it can be used as a general dental glass ionomer cement for applications as has been conventionally used. Particularly, the dental glass ionomer cement composition according to the present invention has a characteristic that, when used for a sealant cement for fluoride prevention, or for a luting cement for cementing a dental prosthesis, which is required to be removed after a certain period of time, it is easily discriminated from a tooth owing to its color difference so that the removal works can be effected readily. Besides, since the dental glass ionomer cement composition according to the present invention can be easily confirmed owing to its color difference, it is also superior as a cement for core construction and a lining cement.

As the fluoroaluminosilicate glass component used in the dental glass ionomer cement composition according to the invention, fluoroaluminosilicate glass powders and the like, which are generally used for dental glass ionomer cements, can be used. Of these, such fluoroaluminosilicate glass powders are preferred which have as the main composition of from 10 to 25% by weight of $Al^{3+}$, from 5 to 30% by weight of $Si^{4+}$, from 1 to 30% by weight of $F^-$, from 0 to 20% by weight of $Sr^{2+}$, from 0 to 20% by weight of $Ca^{2+}$, and from 0 to 10% by weight of alkali metal ions (e.g., $Na^+$, $K^+$ etc.), based on the whole weight of the glass and which are prepared by mixing raw materials containing these components and melting the mixture, and then cooling and pulverizing so as to have a mean particle size of from about 0.02 to 20 µm.

The polycarboxylic acid used in the dental glass ionomer cement composition according to the present invention is a polycarboxylic acid that is used for general dental glass ionomer cements and refers to polymers of an α,β-unsaturated monocarboxylic acid or an α,β-unsaturated dicarboxylic acid. Specifically, it includes copolymers or homopolymers having a weight average molecular weight of from 5,000 to 40,000, of acrylic acid, methacrylic acid, 2-chloroacrylic acid, 3-chloroacrylic acid, aconitic acid, mesaconic acid, maleic acid, itaconic acid, fumaric acid, glutaconic acid, citraconic acid, etc. This component is usually mixed with water and supplied as an aqueous solution, and mixed for use with the powder component. But, it may also be compounded for use into the powder component.

Further, for example, a paste-paste-type material in which a fluoroaluminosilicate glass powder is added with water and a substance having a thickening effect to form a paste, which is then mixed with a polycarboxylic acid solution, and a dental glass ionomer cement processed into a one-paste state by using a microcapsule technique, are available.

The color of a mixture surface of the dental glass ionomer cement composition according to the present invention is required to be a color that is considered of a low reflectance of light. When this color is expressed in terms of an L*a*b* colorimetric system, an L* value is 60 or less in a standard illuminant $D_{65}$.

The L*a*b* colorimetric system was standardized in 1976 by *Commission Internationale de l'Eclairage* (CIE), which is used in Japan as JIS (Japanese Industrial Standards) Z 8729, "Specification of Color of Materials according to CIE1976 (L*a*b*) space and CIE1976 (L*u*v*) space". In this connection, as a light source according to the present invention, a CIE Standard illuminant $D_{65}$ (as defined in JIS Z 8716, "Fluorescent lamp as a simulator of CIE Standard illuminant $D_{65}$ for a visual comparison of surface color-Type and characteristics") is available.

In the L*a*b* colorimetric system, a lightness is defined as L* and expressed by a numerical value of from 0 to 100, in which L*=0 means that the color is complete black, and L*=100 means that the color is complete white. The higher the L* value, or the lower the L* value, the smaller the influence of a hue or a chroma. In case where the L* value exceeds 60, the reflectance of light tends to be high in all hues, and the effect for shortening the time of sensitization to water or the time of initial setting cannot be obtained in the present invention.

In the L*a*b* colorimetric system, a* and b* refer to a hue and a chroma respectively, each of which is expressed by a numerical value of from −60 to 60. Each of a* and b* shows a color direction: a* shows a red direction, and −a* shows a green direction, whereas b* shows a yellow direction, and −b* shows a blue direction. The larger the numerical value of each of a* and b* is, the brighter the color becomes, whereas when the smaller the numerical value of each of a* and b*, the duller the color becomes.

Since no influence of the hue and chroma against the time of sensitization to water or the time of initial setting of the dental glass ionomer cement has been confirmed, the a* and b* values in the L*a*b* colorimetric system are not particularly limited in the present invention.

As the coloring matter that is used in the dental glass ionomer cement composition according to the present invention, any material capable of making the L* value 60 or less can be used regardless of whether it is a pigment or a dye, or of whether it is natural or synthetic. Examples include synthetic coloring matters such as Food Red No. 2, Food Red No. 3, Food Red No. 40, Food Red No. 102, Food Red No. 104, Food Red No. 105, Food Red No. 106, Food Yellow No. 4, Food Yellow No. 5, Food Green No. 3, Food Blue No. 1, and Food Blue No. 2; carotenoid-based coloring matters such as β-carotene and vitamin A; nitro dyes represented by Naphthol Yellow; azoic pigments represented by Oil Yellow and Congo Red; triphenyl dyes represented by Auramine and Fuchsin; indigoid dyes represented by indigo; anthraquinone dyes represented by alizarin; phthalocyanine dyes represented by phthalocyanine; inorganic pigments represented by chromium oxide, barium yellow, emerald green, red oxide; azo pigments represented by Toluidine Red, Dinitroaniline Orange, Chromophthal Yellow, Chromophthal Red, Chromophthal Blue, etc.; phthalocyanine pigments represented by copper phthalocyanine; lake pigments represented by Quinoline Yellow Lake, Food Red No. 2 Aluminum Lake, Food Red No. 3 Aluminum Lake, Food Red No. 40 Aluminum Lake, Food Yellow No. 4 Aluminum Lake, Food Yellow No. 5 Aluminum Lake, Food Green No. 3 Aluminum Lake, Food Blue No. 1 Aluminum Lake, and Food Blue No. 2 Aluminum Lake; condensation pigments represented by anthrapyrimidine yellow, Thioindigo Red, Perinone Red, Perylene Red, and Quinacridone Red; and fluorescent pigments and/or dyes represented by Lumogen Yellow, etc., as well as Methylene Blue, Rhodamine, copper chlorophyll, copper chlorophylline sodium, and the like.

Of these, carotenoid-based coloring matters such as β-carotene and vitamin A, and fluorescent pigments and/or dyes represented by Lumogen Yellow, etc. are preferred from the standpoints of safety and effect. Further, an amount of the coloring matter to be compounded varies depending upon the tendency of color formation and other characteristics of each coloring matter. In order to make the L* value 60 or less in terms of the color of the mixture surface before setting, the coloring matter is preferably contained in an amount ranging from 0.1 to 5% by weight of the composition.

The coloring matter may be contained in advance in any of the respective components of the fluoroaluminosilicate glass, polycarboxylic acid and water, or of the components constituting the dental glass ionomer cement composition in a powder, liquid or paste.

In addition, to the dental glass ionomer cement composition according to the present invention are added known ultraviolet light absorbers, plasticizers, antioxidants, bactericides, surfactants, etc., if desired.

The dental glass ionomer cement composition according to the present invention will be hereunder described in more detail with reference to the following Examples, but it is to be construed that the present invention should not be limited thereto.

All of four dental glass ionomer cements used in the following Examples and Comparative Examples are a dental glass ionomer cement that is set only by a reaction between a fluoroaluminosilicate glass powder and a polycarboxylic acid in the presence of water, and which does not contain a polymerizable monomer.

EXAMPLE 1

One hundred grams of a powder of a commercially available dental glass ionomer cement (a product name: Fuji Ionomer Type III, made by GC Corporation) was added with 7 g of a coloring matter (a product name: β-Carotene, made by Wako Pure Chemical Industries, Ltd.) and colored red. This powder was mixed with a solution (a polycarboxylic acid aqueous solution) of the same product (a product name: Fuji Ionomer Type III, made by GC Corporation) in a proportion of 1.2:1 (on weight basis) and mixed for 30 seconds. The mixture was filled in an acrylic resin-made ring having a diameter of 10 mm and a height of 5 mm, and a transparent celluloid sheet was put on and brought into press contact with the ring. One minute after the start of mixing, irradiation with light was carried out for 20 seconds from the upside of the celluloid sheet by using a visible light irradiator (a product name: GC Labolight LV-II, made of GC Corporation, wavelength: from 400 to 520 nm). Immediately after the irradiation with light, the celluloid sheet was removed, and the sample was immersed in water at 37° C. together with the acrylic resin-made ring. Other samples were irradiated with light in the same manner and allowed to stand in a room temperature for a period of 2 minutes (in this case, 40 seconds after the irradiation with light), 3 minutes, 4 minutes, and sequentially, every one minute after the start of mixing until 30 minutes. Then, the samples were each immersed in water at 37° C. Twenty-four hours later, each sample was taken out from the water, dried and then visually observed for the presence of cloudiness on the sample surface by the sensitization to water. And, a time when the cloudiness of the sample had become not observed after the start of mixing was taken as a time for sensitization to water. Further, the time for sensitization to water was measured in the same manner, except that the light irradiation time was changed to 40 seconds and 60 seconds, respectively. The results obtained are shown in Table 1.

With respect to the dental glass ionomer cement compositions mixed in the above-described method, the irradiation with light was carried out for 20 seconds, 40 seconds, and 60 seconds, respectively. And the time of setting from the start of mixing including the time of irradiation with light was measured in accordance with "5.4 Setting Time Test" of JIS T 6607 (dental glass polyalkenolate cement). The results obtained are also shown in Table 1.

Further, a reflectance of light on the surface of the mixture was measured in the following manner. That is, light was irradiated from a position of 1 m away from a colorimetric light source (a trade name: Sun Reamer, manufactured by Daiwa Lighting Co., Ltd.). And using a photodiode array type spectrophotometer (a trade name: Spectrascan PR650, manufactured by Photo Research Co., Ltd.), a center portion having a diameter of 3 mm of the mixture on a light trap was measured at an angle of about 45° against the surface of the mixture, whereby an L* value of the surface of the mixture was measured. The results obtained are summarized and shown in Table 1.

EXAMPLE 2

One hundred grams of a solution (a polycarboxylic acid aqueous solution) of a commercially available dental glass ionomer cement (a product name: Fuji Ionomer Type II, made by GC Corporation) was added with 1.6 g of a coloring matter (a product name: Chromophthal Yellow, available from Ciba-Geigy Japan Limited)) and colored yellow. The powder was mixed with the solution in a proportion of 2.7:1 (on weight basis), and the sample surface was measured for time of sensitization to water, time of setting and lightness in the same manner as in Example 1. The results obtained are shown in Table 1.

EXAMPLE 3

Two hundred grams of a powder of a commercially available dental glass ionomer cement (a product name: Fuji Lute, made by GC Corporation) was added with 2.2 g of a coloring matter (a product name: Kuchinashi (72), made by Taisho Co., Ltd.) and 1.6 g of a coloring matter (a product name: Bengara, made by Nippon Bengara Kogyo Co., Ltd.) and colored orange. The powder was mixed with a solution in a proportion of 2:1 (on weight basis), and the sample surface was measured for time of sensitization to water, time of setting and lightness in the same manner as in Example 1. The results obtained are shown in Table 1.

Comparative Example 1

The tests were carried out in the same manner as in Example 1 by using a commercially available dental glass ionomer cement (a product name: Fuji Ionomer Type III, made by GC Corporation), except for not containing the coloring matter, thereby measuring the time of sensitization to water, the time of setting and the lightness. The results obtained are shown in Table 1.

Comparative Example 2

The tests were carried out in the same manner as in Example 2 by using a commercially available dental glass ionomer cement (a product name: Fuji IXGP, made by GC Corporation), except for not containing the coloring matter, thereby measuring the time of sensitization to water, the time of setting and the lightness. The results obtained are shown in Table 1.

Comparative Example 3

The tests were carried out in the same manner as in Example 3 by using a commercially available dental glass ionomer cement (a product name: Fuji Ionomer Type II, made by GC Corporation), except for not containing the coloring matter, thereby measuring the time of sensitization to water, the time of setting and the lightness. The results obtained are shown in Table 1.

Comparative Example 4

The tests were carried out in the same manner as in Example 4 by using a commercially available dental glass ionomer cement (a product name: Fuji Lute, made by GC Corporation), except for not containing the coloring matter, thereby measuring the time of sensitization to water, the time of setting and the lightness. The results obtained are shown in Table 1.

TABLE 1

|  | Amount of coloring matter (% by weight) | Time of sensitization to water | | Time of setting | | Lightness ($L^*$) |
|---|---|---|---|---|---|---|
|  |  | Irradiation with light for 20 seconds | Irradiation with light for 30 seconds | Irradiation with light for 20 seconds | Irradiation with light for 30 seconds |  |
| Example 1 | 3.6 | 3 minutes | Since just after the irradiation, no sensitization to water occurred. | 1 minute and 45 seconds | After the irradiation, setting already occurred. | 44.5 |
| Example 2 | 0.4 | 5 minutes | Since just after the irradiation, no sensitization to water occurred. | 2 minutes and 30 seconds | After the irradiation, setting already occurred. | 50.3 |
| Example 3 | 1.2 | 4 minutes | Since just after the irradiation, no sensitization to water occurred | 2 minutes and 00 second | After the irradiation, setting already occurred. | 46.2 |
| Comparative Example 1 | — | 7 minutes | 6 minutes | 3 minutes and 00 second | 2 minutes and 30 seconds | 71.8 |
| Comparative Example 2 | — | 6 minutes | 3 minutes | 3 minutes and 45 seconds | 2 minutes and 15 seconds | 75.9 |
| Comparative Example 3 | — | 9 minutes | 7 minutes | 4 minutes and 00 second | 3 minutes and 00 second | 69.6 |
| Comparative Example 4 | — | 10 minutes | 8 minutes | 4 minutes and 30 seconds | 4 minutes and 00 second | 78.2 |

EFFECTS OF THE PRESENT INVENTION

In the light of the above, it can be confirmed from the Examples and Comparative Examples that in case where the dental glass ionomer cement composition according to the present invention is used in a setting method of a dental glass ionomer cement by means of irradiation with a light to accelerate initial setting, a mixture of a fluoroaluminosilicate glass powder, a polycarboxylic acid and water, it has an effect for further shortening the time of sensitization to water and the time of setting.

In addition, since the dental glass ionomer cement composition according to the present invention, the time for sensitization to water and the time of setting can be shortened by the time for irradiation with light, an operator can arbitrarily set up the operation time. Accordingly, the present invention is very valuable in contributing to the dental remedy.

While the present invention has been described in detail and with reference to specific examples thereof, it will be apparent to one skilled in the art that various changes and modifications can be made therein, without departing from the spirit and scope thereof.

What is claimed is:

1. A dental glass ionomer cement composition comprising a fluoroaluminosilicate powder, a polycarboxylic acid and a coloring matter, a color of which is specified such that an L* value, when expressed in an L*a*b* colorimetric system in a standard illuminant $D_{65}$, is 60 or less, wherein said glass ionomer composition does not contain a polymerizable monomer, and said coloring matter is Food Red No. 104, Food Red No. 105, Food Red No. 106, β-carotene, vitamin A, Auramine, Fuchsin, chromium oxide, barium yellow, emerald green, red oxide, Toluidine Red, Dinitroaniline Orange, Chromophthal Yellow, Chromophthal Red, Chromophthal Blue, copper phthalocyanine, Quinoline Yellow Lake, anthrapyrimidine yellow, Thioindigo Red, Perinone Red, Perylene Red, Quinacridone Red, Lumogen Yellow, Methylene Blue, Rhodamine, copper chlorophyll or copper chlorophylline sodium.

2. The dental glass ionomer cement composition according to claim 1, wherein said coloring matter is β-carotene, Vitamin A or Lumogen Yellow.

3. The dental glass ionomer cement composition according to claim 1, wherein said coloring matter is red oxide.

4. The dental glass ionomer cement composition according to claim 1, wherein said coloring matter is chromophthal yellow.

* * * * *